US007846918B2

(12) United States Patent
Pariza et al.

(10) Patent No.: US 7,846,918 B2
(45) Date of Patent: Dec. 7, 2010

(54) EXEMESTANE COMPOUNDS, COMPOSITIONS AND RELATED METHODS OF USE

(75) Inventors: Richard J. Pariza, Zion, IL (US); James G. Yarger, Cedarburg, WI (US)

(73) Assignee: Endece, LLC, Mequon, WI (US)

( * ) Notice: Subject to any disclaimer, the term of this patent is extended or adjusted under 35 U.S.C. 154(b) by 0 days.

(21) Appl. No.: 11/541,987

(22) Filed: Oct. 2, 2006

(65) Prior Publication Data

US 2007/0088013 A1   Apr. 19, 2007

Related U.S. Application Data

(60) Provisional application No. 60/722,204, filed on Sep. 30, 2005.

(51) Int. Cl.
*A61K 31/56* (2006.01)
*C07J 1/00* (2006.01)

(52) U.S. Cl. ........................ 514/177; 552/640
(58) Field of Classification Search ................ 514/177; 552/640

See application file for complete search history.

(56) References Cited

U.S. PATENT DOCUMENTS 4,808,616 A   2/1989   Buzzetti et al.

FOREIGN PATENT DOCUMENTS

JP   07-215992   8/1995
WO   2005070951   8/2005
WO   WO 2005/070951 * 8/2005

OTHER PUBLICATIONS

Vippagunta et al. (Advanced Drug Delivery Reviews, 48 (2001), pp. 3-26).*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Numazawa, M; Ando, M; and Zennyoji, R; Studies on the Catalytic Function of Aromatase: Aromatization of 6-Alkoxy-Substituted Androgens; Journal of Steroid Biochemistry & Molecular Biology, 2002, 65-73, vol. 82.
Sanderson, T; and Van Den Berg, M; Interactions of Xenobiotics with the Steroid Hormone Biosynthesis Pathway; Pure Appl. Chem. 2003, 1957-1971, vol. 75, Nos. 11-12.
Gorlitzer, K; Bonnekessel, C; Jones, PG; and Kaufmann, G.; Unerwartete Bildung eines Estron-Derivates aus Androsta-1,4-dien-3,17-dion; Pharmazie, 2002, 808-810, vol. 57.
Mitsuteru Numazawa, Momoko Ando, Yoko Watari, Takako Tominaga, Yasuko Hayata, Akiko Yoshimura, Structure-activity relationship of 2-, 4-, or 6-substituted estrogens as aromatase inhibitors, The Journal of Steroid Biochemistry and Molecular Biology, 96, 2005 51-58, Elsevier Ltd.
Goerlitzer, Klaus, et al. Exemestane-synthesis and analysis, Deutsche Apotheker Zeitung; ISSN; 0011-9857, vol. 145, No. 37, Sep. 19, 2005.

* cited by examiner

*Primary Examiner*—Barbara P Badio
(74) *Attorney, Agent, or Firm*—Reinhart Boerner Van Deuren s.c.

(57) ABSTRACT

6-Methyloxaalkyl exemestane compounds and related compositions, as can be used, chemotherapeutically, to inhibit growth and proliferation of cancer cells.

17 Claims, 2 Drawing Sheets

EXEMESTANE COMPOUNDS, COMPOSITIONS AND RELATED METHODS OF USE

This application claims priority benefit from application Ser. No. 60/722,204 filed Sep. 30, 2005, the entirety of which is incorporated herein by reference.

BACKGROUND OF THE INVENTION

Abnormal cell proliferation is usually characterized by an increased rate of division and in some cases uncontrolled growth. One example of a proliferative cell disorder is a tumor. In addition to posing a serious health risk in and of themselves, primary malignant tumors are particularly problematic given their tendency to invade surrounding tissues and metastasize to distant organs in the body. To date, the most frequently used methods for treating neoplasia, especially solid tumor forms of neoplasia, include surgical procedures, radiation therapy, drug therapies, and combinations of the foregoing.

Drug therapy for breast cancer may include the administration of exemestane to a patient. Product information available on-line from the U.S. Food and Drug Administration describes exemestane as an irreversible, steroidal aromatase inactivator. Exemestane (which is sold under the AROMASIN® trademark), is chemically described as 6-methylenandrosta-1,4-diene-3,17-dione. Its molecular formula is $C_{20}H_{24}O_2$ and its structural formula is as follows:

Among other things, exemestane lowers circulating estrogen concentrations in postmenopausal women thereby providing a treatment for some postmenopausal patients with hormone-dependent breast cancer.

U.S. Pat. Nos. 4,808,616, and 4,904,650 describe 6-alkylidenandrosta-1,4-diene-3,17-dione derivatives, such as exemestane, and methods of making them. U.S. Pat. No. 4,876,045 teaches a method of preparing 6-methylene derivatives of androsta-1,4-diene-3,17-diones by reacting a 17-hydroxy precursor with formaldehyde and an amine, and then oxidizing the resulting compound. U.S. Pat. No. 4,990,635 teaches a process for making 6-methylene derivatives of androsta-1,4-diene-3,17-diones by reacting androsta-3,5-diene-17-one with formaldehyde and an amine, and then dehydrogenating the resulting compound.

The preparation of intermediates that may be useful in preparing exemestane is also described in the literature. In U.S. Pat. No. 3,274,176, there is described a process for making 1,3-dipyrrolidyl-Δ3,5-androstadiene-17-one in which Δ1,4-androstadiene-3,17-dione is refluxed with pyrrolidine and the residue is crystallized in methanol to obtain 1,3-dipyrrolidyl-Δ3,5-androstadiene-17-one. In German patent DD 258820, 6-hydroxymethyl-androsta-1,4-diene-3,17-dione is prepared from androsta-1,4-diene-3,17-dione via 1,3-dipyrrolidinoandrosta-3,5-dien-17-one. A solution of 1,3-dipyrrolidinoandrosta-3,5-dien-17-one in benzene-ethanol is stirred with aqueous formaldehyde (HCHO) until the reaction is complete. Co-pending international application no. PCT/US2005/001248 filed Jan. 14, 2005 (PCT Publication Number WO 2005/070951) also describes the preparation of intermediates that are useful in preparing exemestane, such application as is incorporated herein by reference, in its entirety.

The clinical pharmacology in this exemestane product information states that the mechanism of action for breast cancer cell growth may be estrogen-dependent. Aromatase is described as the principal enzyme that converts androgens to estrogens both in pre- and postmenopausal women. It is reported that the principal source of circulating estrogens in postmenopausal women is from conversion of adrenal and ovarian androgens (androstenedione and testosterone) to estrogens (estrone and estradiol) by the aromatese enzyme. Estrogen deprivation through aromatase inhibition is described as an effective and selective treatment for some postmenopausal patients with hormone-dependent breast cancer. Exemestane as an irreversible, steroidal aromatase inactivator is believed to act as a false substrate for the aromatase enzyme, and processed to an intermediate that binds irreversibly to the active site of the enzyme causing its inactivation. Exemestane lowers circulating estrogen concentrations in postmenopausal women thereby providing a treatment for some postmenopausal patients with hormone-dependent breast cancer.

However, a need still exists to identify new and effective agents for treating cancer.

SUMMARY OF THE INVENTION

In light of the foregoing, it is an object of the present invention to provide chemotherapeutic compounds, compositions and/or methods for their use and preparation, thereby overcoming various deficiencies and shortcomings of the prior art, including those outlined above. It will be understood by those skilled in the art that one or aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to provide one or more compounds, compositions, and/or methods to more broadly treat a cancer disease state, in particular such a state or condition not hormone and/or estrogen dependent.

It can be another object of the present invention to provide one or more compounds, compositions, and/or methods to deleteriously affect cancer cellular growth or proliferation without restriction to aromatase inhibition.

It can be another object of the present invention to provide more generally, without restriction to any one compound or composition, use of an exemestane 6-methylene substituent to effect results of the sort described herein.

Other objects, features, benefits and advantages of the present invention will be apparent from this summary and the following descriptions of certain embodiments, and will be readily apparent to those skilled in the art having knowledge of various chemotherapeutic compounds, methods and/or modes of operation. Such objects, features, benefits, and advantages will be apparent from the above as taken into conjunction with the accompanying examples, data, figures and all reasonable inferences to be drawn therefrom, alone or with consideration of the references incorporated herein.

In part, the present invention can be directed to a chemotherapeutic compound of a formula In such a compound $R_1$, $R_2$, $R_3$ and $R_4$ can be independently selected from H alkyl, substituted alkyl and halogen moieties. Regardless, $R_5$, can be selected from alkyl and substituted alkyl moieties. Such a compound can be selected from any one or more of the available enantiomers, other stereochemical isomers, hydrates, solvates, tautomers and possible salts thereof. In certain embodiments, $R_5$ can be selected from $C_1$ to about $C_6$ alkyl and $C_1$ to about $C_6$ substituted alkyl moieties. In certain such embodiments, $R_5$ can be methyl and, optionally such a compound can be present as the S enantiomer.

In part, the present invention can also be directed to a pharmaceutical composition. Such a composition can comprise one or more compounds selected from those discussed above, illustrated below or otherwise inferred herein, and combinations thereof. In certain embodiments, such a composition can comprise a pharmaceutically-acceptable carrier component. Without limitations such a composition can comprise a racemic mixture of compounds. In certain such embodiments, such a compound can be present as the S enantiomer, and $R_5$ can be selected from $C_1$ to about $C_6$ allyl and $C_1$ to about $C_6$ substituted alkyl moieties.

In part, this invention can also be directed to a method of using an exemestane 6-methylene substituent to affect cancer growth. Such a method can comprise providing a compound with an exemestane core structure comprising a methyloxaalkyl substituent at the 6-position of such a core structure; and contacting a cancer growth with such a compound. In certain embodiments the alkyl moiety of the 6-methylene substituent call be selected from $C_1$ to about $C_6$ alkyl and $C_1$ to about $C_6$ substituted alkyl moieties. In certain such embodiments the alkyl moiety can be methyl, and the compound can be present as the S enantiomer. Regardless, such a method can comprise contact with and affect estrogen(−) and/or aromatase(+) cell lines.

For purposes of the present compounds, compositions and/or methods, the following, unless otherwise indicated, will be understood as having the meaning ascribed thereto by those skilled in the art or as otherwise indicated with respect thereto: "exemestane core structure" means a structure comprising a 3,17-dione-1,4-diene fused ring structure. Representative structures, without regard to substitution, or to stereochemistry at the 6-position include but are not limited to where $R_1$, $R_2$, $R_3$ and $R_4$ can be H, alkyl, substituted alkyl, halogen, etc., together with tautomers thereof.

In part, this invention can also be directed to a method of treating a subject and/or inhibiting growth of cancer cells. Such a method can comprise providing a subject/growth of cancer cells; and contacting such a growth with one or more compounds selected from compounds discussed above, illustrated below or otherwise inferred herein, and combinations thereof. Such a compound can be in an amount at least partially sufficient to inhibit growth of such cancer cells, such inhibition substantially without aromatase inhibition and/or in an amount or at a concentration substantially insufficient to inhibit aromatase activity, such insufficiency as can be determined by comparison with exemestane.

In certain embodiments, without limitation, such a compound can be of a formula (A)

wherein $R_1$, $R_2$, $R_3$ and $R_4$ can be independently selected from H, alkyl, substituted alkyl and halogen moieties. In certain such embodiments, $R_5$ can be selected from alkyl and substituted alkyl moieties. Regardless, such compounds can be selected from any one or combination of possible enantiomers, hydrates, solvates, tautomers and salts of such compounds.

In certain embodiments, such a method can be effected with one or more compounds, such as wherein $R_5$ can be selected from $C_1$ to about $C_6$ alkyl and $C_1$ to about $C_6$ substituted alkyl moieties. As illustrated below, $R_5$ can be methyl. Regardless, any such compound or combinations thereof can be present in a pharmaceutical composition. As illustrated below, such a method can be used to inhibit breast, lung, colon, prostate, ovarian and pancreatic cancerous growths and/or cell lines.

In part, the present invention can also be directed to a method of using a 6-methyloxamethyl exemestane derivative to inhibit growth of cancer cells. Such a method can comprise providing cancer cell growth; and contacting such cells or growth with a methyloxamethyl compound selected from one or more compounds discussed above, illustrated below or otherwise inferred herein, and combinations thereof. Such a compound can be in an amount at least partially sufficient to inhibit such cellular growth, such inhibition substantially without aromatase inhibition and/or in an amount or at a concentration substantially insufficient to inhibit aromatase activity, such insufficiency as can be determined by comparison with exemestane. In certain embodiments, such a compound can be of a formula

(A)

wherein each of $R_1$, $R_2$, $R_3$, and $R_4$, independently, is hydrogen, halogen or alkyl, and $R_5$ is alkyl.

One specific non-limiting example compound of Formula (A) has the Formula (B) below:

(B)

(B)

Such a compound can be used to inhibit cancer cellular or tumor growth associated with breast, lung, colon, prostate, ovarian and pancreatic cancers.

In part, the present invention can also be directed to a method for preparing an oxaalkyl derivative of exemestane. Such a method can comprise providing a 3,5-diene derivative of (+)-androsta-1,4-diene-3,17-dione; formylating such a diene at the 6-position thereof, to provide a hydroxymethyl derivative; and alkylating the hydroxymethyl derivative. In certain embodiments, the aforementioned 3,5-diene derivative can be prepared by reaction of pyrrolidine with the 3,17-dione under appropriate catalytic and reaction conditions. Various oxaalkyl derivatives, in accordance with this invention, are limited only by choice of alkylating agent, such derivatives as would be understood by those skilled in art made aware of this invention, as available through synthetic procedures of the sort described herein or straight-forward modifications thereof, such modifications as would also be understood by those skilled in the art. Accordingly, without limitation, various $C_1$ to about $C_6$ alkyl and substituted alkyl (e.g., $C_1$ to about $C_6$ linear, substituted linear, branched and substituted branched alkyl, such substituents as would be understood in the art) reagents can be used as described herein to prepare the corresponding oxaalkyl derivatives.

More specifically, showing various stereochemical relationships, such a compound B can be represented as The compound of Formula (B) can be referred to as "6S" or "Exemestane 6S".

Figure 1:
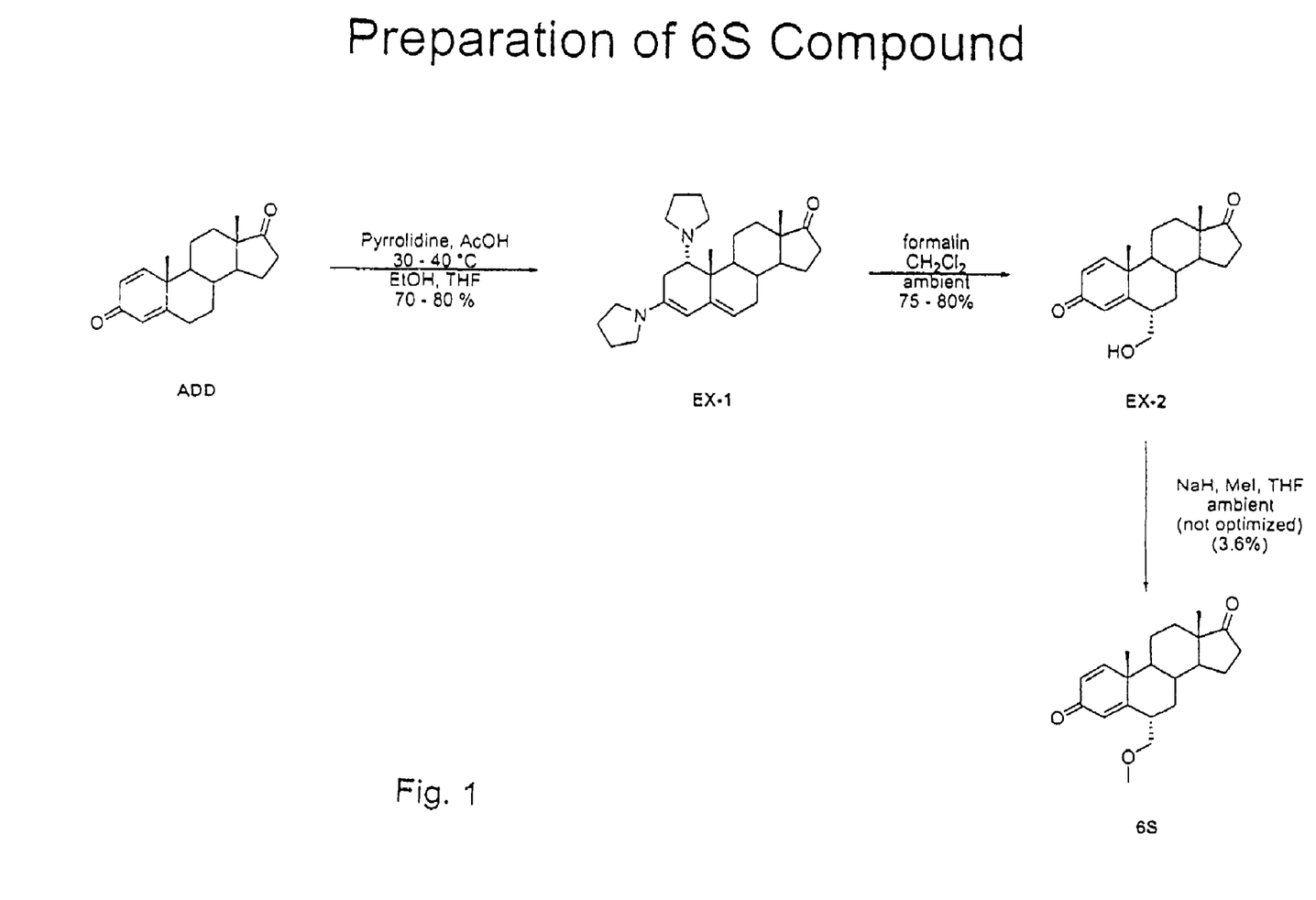
FIG. 1 shows a reaction scheme for preparing one example exemestane derivative according to the invention.

Looking at FIG. 1, the compound of formula (B) can be prepared by first preparing 1,3-dipyrrolidinoandrosta-3,5-diene-17-one (EX-1) from (+)-androsta-1,4-diene-3,17-dione (ADD). One set of conditions utilizes (+)-androsta-1,4-diene-3,17-dione (ADD), 12.2 equivalents pyrrolidine, catalytic acetic acid, denatured ethanol (95/5 ethanol/methanol) and 6-7% tetrahydrofuran (volume basis of total volume of ethanol and pyrrolidine) with heating to 30-40° C. for a minimum of 16 hours. Once the ADD content is less than 3% by HPLC area, becomes static or EX-1 begins to revert to ADD, the reaction mixture is cooled to 5±5° C., collected and washed

DETAILED DESCRIPTION OF CERTAIN EMBODIMENTS

In one aspect, this invention provides a method for inhibiting growth of cells of a cancer or a tumor. In such a method, the cells are exposed to or contacted with a compound of Formula (A) or pharmaceutically acceptable salts or hydrates thereof:

with cold denatured ethanol. Yields are typically 70- 80% on a dry basis with purities typically 90-95% by HPLC area percent.

Next, 6-hydroxymethyl-androsta-1,4-diene-3,17-dione (EX-2) is prepared from 1,3-dipyrrolidinoandrosta-3,5-diene-17-one (EX-1). One set of conditions for the preparation employ 1 equivalent 1,3-dipyrrolidinoandrosta-3,5-diene-17-one (EX-1) and 2.6 equivalents formalin (formaldehyde) in 10 mL dichloromethane/g of EX-1 at room temperature. Workup consists of acidification of the reaction mixture to a pH of about 2, dilution with 2% sulfuric acid (aqueous, volume/volume basis) and removal of the organic layer which is then washed with 2% sulfuric acid (vol/vol) and 1:1 water/brine. Solvent exchange into toluene (approximately 10 mL/g theory EX-2) is then carried out and the product crystallizes as toluene exchange transpires. The product is collected, washed and dried to provide 6-hydroxymethyl-androsta-1,4-diene-3,17-dione (EX-2) in yields of typically 75-80%. Purity is usually 96% or greater by HPLC area percent. Next, the 6-hydroxymethyl-androsta-1,4-diene-3,17-dione (EX-2) may be treated as shown in FIG. 1 to prepare the 6S compound, which is Formula (B) above.

In another aspect of such a method the cells are exposed to a compound of Formula (C) or pharmaceutically acceptable salts or hydrates thereof:

(C)

wherein each of $R_1$, $R_2$, $R_3$, $R_4$, independently, is hydrogen, halogen or alkyl, and $R_5$ is alkyl.

One specific non-limiting example compound of Formula (C) has the Formula (D) below:

(D)

Figure 2:
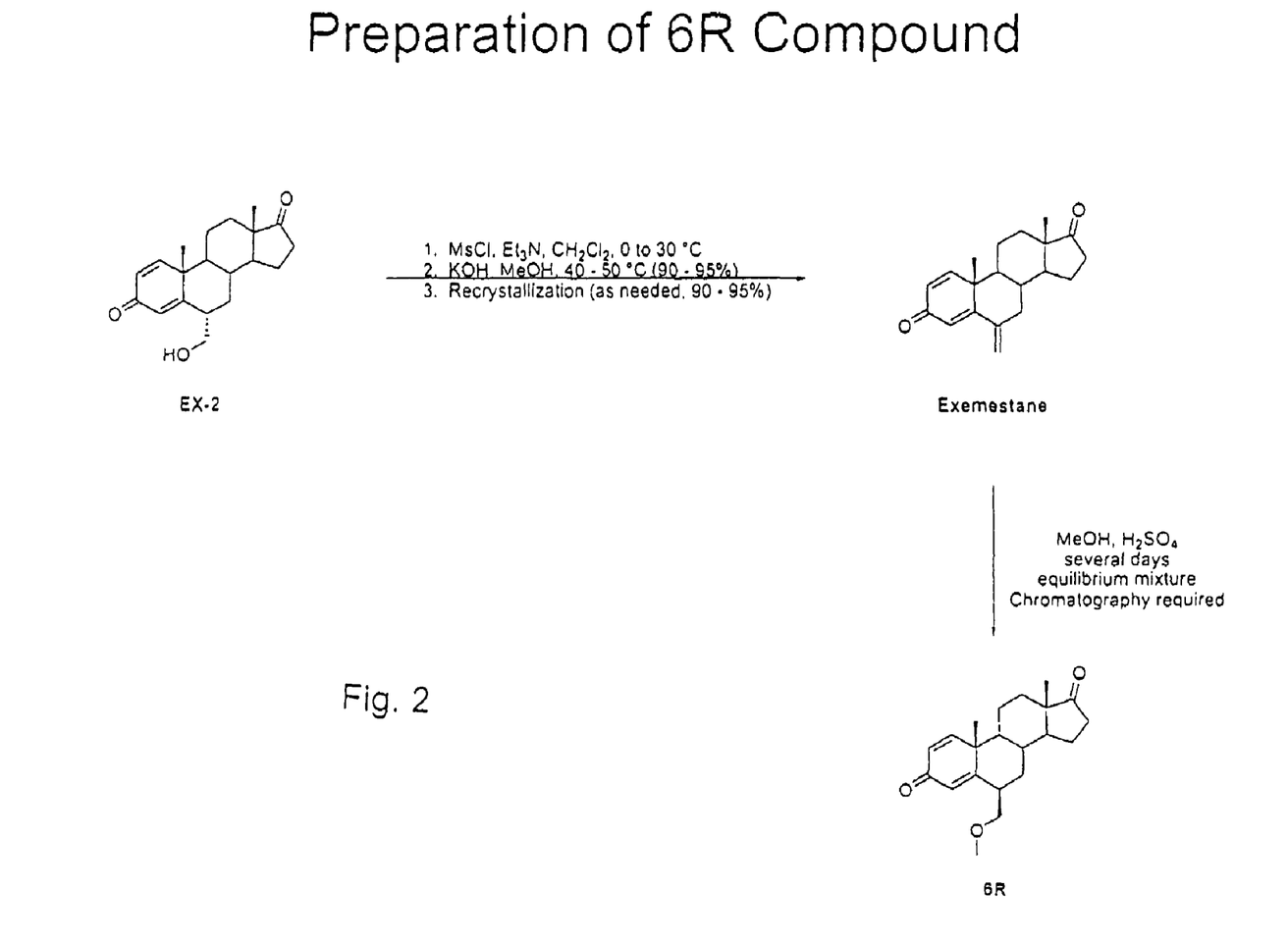
FIG. 2 shows a reaction scheme for preparing another example exemestane derivative according to the invention.

More specifically showing various stereochemical relationships, such a compound D can be represented as The compound of Formula (D) can be referred to as "6R" or "Exemestane 6R". Looking at FIG. 2, the compound of formula (D) can be prepared by reacting 6-hydroxymethyl-androsta-1,4-diene-3,17-dione (EX-2) as shown in FIG. 2 to produce exemestane and then reacting the exemestane as shown in FIG. 2 to produce the 6R compound, which is Formula (D) above.

To treat an individual/subject, an effective amount of one or more of the present compounds, or a pharmaceutically-acceptable salt thereof, is administered so as to be exposed to or contact cancer cells or a tumor. Effective dosage forms, modes of administration and dosage amounts may be determined empirically, and making such determinations is within the skill of the art. It is understood by those skilled in the art that the dosage amount will vary with the activity of the particular compound employed, course and/or progression of the disease state, the route of administration, the rate of excretion of the compound, the duration of the treatment, the identity of any other drugs being administered to the subject, age, size and like factors well known in the medical arts. In general, a suitable daily dose will be that amount which is the lowest dose effective to produce a therapeutic effect. The total daily dosage will be determined by an attending physician within the scope of sound medical judgment. If desired, the effective daily dose of such a compound, or a pharmaceutically-acceptable variation or salt thereof, maybe administered as two, three, four, five, six or more sub-doses, administered separately at appropriate intervals throughout the day. Treatment includes mitigation, as well as elimination, of the disease state.

Compounds of this invention may be administered to patient for therapy by any suitable route of administration, including orally, nasally, rectally, intravaginally, parenterally, intracisternally and topically, as by powders, ointments or drops, including buccally and sublingually. The preferred routes of administration are orally and parenterally.

While it is possible for the active ingredient(s) (one or more compounds of this invention and/or pharmaceutically-acceptable salts thereof, alone or in combination with another therapeutic agent) to be administered alone, it is preferable to administer the active ingredient(s) as a pharmaceutical formulation (composition). The pharmaceutical compositions of the invention comprise the active ingredient(s) in admixture with one or more pharmaceutically-acceptable carriers and, optionally, with one or more other compounds, drugs or other materials. Each carrier must be "acceptable" in the sense of being compatible with the other ingredients of the formulation and not injurious to the patient.

Pharmaceutical formulations of the present invention include those suitable for oral, nasal, topical (including buccal and sublingual), rectal, vaginal and/or parenteral administration. Regardless of the route of administration selected, the active ingredient(s) are formulated into pharmaceutically-acceptable dosage forms by conventional methods known to those of skill in the art.

The amount of the active ingredient(s) which will be combined with a carrier material to produce a single dosage form will vary depending upon the host being treated, the particular mode of administration and all of the other factors described above. The amount of the active ingredient(s) which will be combined with a carrier material to produce a single dosage form will generally be that amount of the active ingredient(s) which is the lowest dose effective to produce a therapeutic effect.

Methods of preparing pharmaceutical formulations or compositions include the step of bringing the active ingredient(s) into association with the carrier and, optionally, one or more accessory ingredients. In general, the formulations are prepared by uniformly and intimately bringing the active ingredient(s) into association with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of the active ingredient(s). The active ingredient(s) may also be administered as a bolus, electuary or paste.

In solid dosage forms of the invention for oral administration (capsules, tablets, pills, dragees, powders, granules and the like), the active ingredient(s) is/are mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethyl-cellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient(s) moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient(s) therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient(s) can also be in microencapsulated form.

Liquid dosage forms for oral administration of the active ingredient(s) include pharmaceutically-acceptable emulsions, microemulsions, solutions, suspensions, syrups and elixirs. In addition to the active ingredient(s), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents. Suspensions, in addition to the active ingredient(s), may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing the active ingredient(s) with one or more suitable nonirritating excipients or carriers comprising, for example, cocoa butter, polyethylene glycol, a suppository wax or salicylate and which is solid at room temperature, but liquid at body temperature and, therefore, will melt in the rectum or vaginal cavity and release the active ingredient(s). Formulations of the present invention which are suitable for vaginal administration also include pessaries, tampons, creams, gels, pastes, foams or spray formulations containing such carriers as are known in the art to be appropriate.

Dosage forms for the topical or transdermal administration of the active ingredient(s) include powders, sprays, ointments, pastes, creams, lotions, gels, solutions, patches and inhalants. The active ingredient(s) may be mixed under sterile conditions with a pharmaceutically-acceptable carrier, and with any buffers, or propellants which may be required.

The ointments, pastes, creams and gels may contain, in addition to the active ingredient(s), excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the active ingredient(s), excipients such as lactose, talc, silicic acid, aluminum hydroxide, calcium silicates and polyamide powder, or mixtures of these substances. Sprays can additionally contain customary propellants such as chlorofluorohydrocarbons and volatile unsubstituted hydrocarbons, such as butane and propane.

Transdermal patches have the added advantage of providing controlled delivery of the active ingredient(s) to the body. Such dosage forms can be made by dissolving, dispersing or otherwise incorporating the active ingredient(s) in a proper medium, such as an elastomeric matrix material. Absorption enhancers can also be used to increase the flux of the active ingredient(s) across the skin. The rate of such flux can be controlled by either providing a rate-controlling membrane or dispersing the active ingredient(s) in a polymer matrix or gel.

Pharmaceutical compositions of this invention suitable for parenteral administration comprise the active ingredient(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monostearate and gelatin.

In some cases, in order to prolong the effect of the active ingredient(s), it is desirable to slow the absorption of the drug from subcutaneous or intramuscular injection. This may be accomplished by the use of a liquid suspension of crystalline or amorphous material having poor water solubility. The rate of absorption of the active ingredient(s) then depends upon its/their rate of dissolution which, in turn, may depend upon crystal size and crystalline form. Alternatively, delayed absorption of parenterally-administered active ingredient(s) is accomplished by dissolving or suspending the active ingredient(s) in an oil vehicle.

Injectable depot forms are made by forming microencapsule matrices of the active ingredient(s) in biodegradable polymers such as polylactide-polyglycolide. Depending on the ratio of the active ingredient(s) to polymer, and the nature of the particular polymer employed, the rate of release of the active ingredient(s) can be controlled. Examples of other biodegradable polymers include poly(orthoesters) and poly(anhydrides). Depot injectable formulations are also prepared by entrapping the active ingredient(s) in liposomes or microemulsions which are compatible with body tissue. The injectable materials can be sterilized for example, by filtration through a bacterial-retaining filter.

The formulations may be presented in unit-dose or multi-dose sealed containers, for example, ampoules and vials, and may be stored in a lyophilized condition requiring only the addition of the sterile liquid carrier, for example water for injection, immediately prior to use. Extemporaneous injection solutions and suspensions maybe prepared from sterile powders, granules and tablets of the type described above.

The pharmaceutical compositions of the present invention may also be used in the form of veterinary formulations, including those adapted for the following: (1) oral administration, for example, drenches (aqueous or nonaqueous solutions or suspensions), tablets, boluses, powders, granules or pellets for admixture with feed stuffs, pastes for application to the tongue; (2) parenteral administration, for example, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam.

Examples of the Invention

The following non-limiting examples and data illustrate various aspects and features relating to the compounds, compositions and/or methods of the present invention, including the use of a range of methyloxaaklyl derivatives of exemestane, as are available through the synthetic methodologies described herein. In comparison with the prior art, the present compounds, compositions and/or methods provide results and data which are surprising, unexpected and contrary thereto. While the utility of this invention is illustrated through the use of several compounds and moieties incorporated therein, it will understood be those skilled in the art that comparable results are obtainable with various other compounds, compositions and related methods, as are commensurate with the scope of this invention.

EXAMPLE 1

Activity Of 6-Methyloxamethyl Exemestane Compounds Against Cancer Cell Lines. Cancer-derived cell lines were used for the following growth inhibition assay. The ability of the compound of Formula (B) above and the compound of Formula (D) above to inhibit cancer-derived cell growth was compared to exemestane as a control.

Cell viability is determined using the MTS assay. This calorimetric procedure measures conversion of the MTS reagent (a tetrazoleum salt) to formazan by living cells. Formazan production is quantified by spectrophotometric measurement at 490 nm and is proportional to viable cell number. Cells are cultured and treated. Following treatment, 100 µl of growth medium is removed and cells incubated with 20 µl CellTiter 96® AQ$_{ueous}$ One Solution Reagent (1.9 mg/ml in PBS, pH 6.0) for 1-3 hours at 37° C. Absorbance (OD) values are measured using a µQuant microplate reader at a single wavelength of 490 nm. The data were measured as the 50% inhibitory dose (IC$_{50}$) and are reported in Table 1 below.

TABLE 1

| | | Mean IC$_{50}$ Values* | | |
| --- | --- | --- | --- | --- |
| Cell Line | Cancer type | Exemestane 6S Formula (B) | Exemestane 6R Formula (D) | Exemestane (control) |
| MDA-MB-231 | Breast | >200 µM | 77 µM | 64 µM |
| MCF-7 | Breast | >200 µM | >200 µM | 96 µM |
| MV 522 | Lung | >200 µM | 95 µM | 103 µM |
| NIH: H23 | Lung | >200 µM | 106 µM | 50 µM |
| HT-29 | Colon | >200 µM | 110 µM | 103 µM |
| PC-3 | Prostrate | >200 µM | 108 µM | 105 µM |

TABLE 1-continued

| | | Mean IC$_{50}$ Values* | | |
|---|---|---|---|---|
| Cell Line | Cancer type | Exemestane 6S Formula (B) | Exemestane 6R Formula (D) | Exemestane (control) |
| SK-OV-3 | Ovarian | >200 μM | 106 μM | 78 μM |
| NIH: OVCAR-3 | Ovarian | >200 μM | 54 μM | 73 μM |
| Capan-1 | Pancreas | >200 μM | 176 μM | 98 μM |
| Capan-2 | Pancreas | >200 μM | 104 μM | 94 μM |

*All data represent the mean of 2 independent trials.

Additional assays were performed to evaluate the growth-inhibiting activity of the compound of Formula (B) above and the compound of Formula (D) compared to exemestane as a control. The percent of cell growth inhibited at a dose of 200 μM is reported in Table 2 below.

TABLE 2

| | | Mean Percent Response at 200 μM | | |
|---|---|---|---|---|
| Cell Line | Cancer type | Exemestane 6S Formula (B) | Exemestane 6R Formula (D) | Exemestane (control) |
| MDA-MB-231 | Breast | 21% | 95% | 67% |
| MCF-7 | Breast | 0% | 56% | 68% |
| MV 522 | Lung | 19% | 96% | 79% |
| NIH: H23 | Lung | 12% | 65% | 81% |
| HT-29 | Colon | 8% | 80% | 75% |
| PC-3 | Prostate | 0% | 78% | 67% |
| SK-OV-3 | Ovarian | 0.3% | 98% | 85% |
| NIH: OVCAR-3 | Ovarian | 6% | 78% | 88% |
| Capan-1 | Pancreas | 5% | 28% | 74% |
| Capan-2 | Pancreas | 15% | 46% | 56% |

Table 3 below provides the cell line information.

TABLE 3

| Cell Line | Cancer type | Histology/Characteristics |
|---|---|---|
| MDA-MB-231 | Breast | Adenocarcinoma/ER(−) Aromatase (+) |
| MCF-7 | Breast | Adenocarcinoma/ER(+) Aromatase (−) |
| MV 522 | Lung | Metastatic NSCLC/ER(?) |
| NIH: H23 | Lung | Metastatic NSCLC/ER(+) |
| HT-29 | Colon | Adenocarcinoma/ER(−) |
| PC-3 | Prostate | Adenocarcinoma/ER(−) |
| SK-OV-3 | Ovarian | Adenocarcinoma/ER(−) Aromatase (+) |
| NIH: OVCAR-3 | Ovarian | Adenocarcinoma/ER(+) Aromatase (−) |
| Capan-1 | Pancreas | Adenocarcinoma/ER(+) |
| Capan-2 | Pancreas | Adenocarcinoma/ER(−) |

The compound of Formula (D) (6R) demonstrates excellent activity against a variety of cancer cell lines (95-98% inhibition—see Table 2). By comparison, the exemestane (control) shows marginal activity against the same cell lines. In addition, under the conditions and protocols employed, the data consistently shows that Formula (B) (exemestane 6S) works best against cell lines that are estrogen (−) and/or aromatase (+), as compared to cell lines that are estrogen (+) and aromatase (−).

Thus, the 6-methylene substituted exemestane compounds described herein have been discovered to be able to inhibit the growth of cancer cells. This indicates that the exemestane derivatives described herein are useful for cancer treatments and therapies when provided to a patient either individually or in various combinations with each other or with other compounds which have anticancer or antitumor activity. In light of the ability of the exemestane derivatives described herein to inhibit various types of cancer cells, exemestane derivatives described herein are useful as antitumor or antiproliferative agents for cancer chemotherapeutic applications.

Although the present invention has been described with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

We claim:

1. A chemotherapeutic compound selected from compounds of a formula wherein each of $R_1$, $R_2$, $R_3$ and $R_4$ is independently selected from H, alkyl, substituted alkyl and halogen moieties; and $R_5$ is selected from alkyl and substituted alkyl moieties; and enantiomers, tautomers and salts thereof.

2. The compound of claim 1 wherein $R_5$ is selected from $C_1$-$C_6$ alkyl and $C_1$-$C_6$ alkyl substituted alkyl moieties.

3. The compound of claim 2 wherein $R_5$ is methyl.

4. A pharmaceutical composition comprising a compound selected from compounds of a formula wherein each of $R_1$, $R_2$, $R_3$ and $R_4$ is independently selected from H, alkyl, substituted alkyl and halogen moieties; and $R_5$ is selected from alkyl and substituted alkyl moieties; and enantiomers, tautomers and salts thereof; and a pharmaceutically-acceptable carrier.

5. The composition of claim 4 wherein $R_5$ is selected from $C_1$-$C_6$ alkyl and $C_1$-$C_6$ alkyl substituted alkyl moieties.

6. The composition of claim 5 wherein $R_5$ is methyl.

7. A method of using an exemestane 6-methyleneoxaalkyl substituent to reduce cancer growth, said method comprising:
providing a compound with an exemestane core structure comprising a methyleneoxaalkyl substituent at the 6-position of said core structure; and
contacting a cancer growth with said compound, said cancer growth selected from breast, lung, colon, prostate, ovarian and pancreatic cancer growths.

8. The method of claim 7 wherein the alkyl moiety of said 6-methylene substituent is selected from $C_1$-$C_6$ alkyl and $C_1$-$C_6$ alkyl substituted alkyl moieties.

9. The method of claim 8 wherein said alkyl moiety is methyl.

10. The method of claim 9 wherein said compound is the R enantiomer.

11. A method of reducing growth of cancer cells, said method comprising:
providing a growth of cancer cells, said cancer growth selected from breast, lung, colon, prostate, ovarian and pancreatic cancer growths; and
contacting said cells with a compound selected from compounds of a formula wherein each of $R_1$, $R_2$, $R_3$ and $R_4$ is independently selected from H, alkyl, substituted alkyl and halogen moieties; and $R_5$ is selected from alkyl and substituted alkyl moieties; and enantiomers, tautomers and salts thereof, said compound in an amount at least partially sufficient to reduce said growth.

12. The method of claim 11 wherein said compound is of a formula

13. The method of claim 12 wherein $R_5$ is selected from $C_1$-$C_6$ alkyl and $C_1$-$C_6$ alkyl substituted alkyl moieties.

14. The method of claim 13 wherein $R_5$ is methyl.

15. The method of claim 11 wherein said compound is in a pharmaceutical composition.

16. A method of using a 6-methyloxamethyl exemestane compound to treat cancer cells, said method comprising:
providing a growth of cancer cells, said cancer growth selected from breast, lung, colon, prostate, ovarian and pancreatic cancer growths; and
contacting said cells with a methyloxamethyl compound selected from compounds of a formula, wherein each of $R_1$, $R_2$, $R_3$ and $R_4$ is independently selected from H, alkyl, substituted alkyl and halogen moieties; and $R_5$ is selected from alkyl and substituted alkyl moieties; and enantiomers, tautomers and salts thereof, said compound in an amount at least partially sufficient to treat said growth.

17. The method of claim 16 wherein said compound is of a formula

* * * * *